United States Patent [19]

Shelton

[11] 4,202,879
[45] May 13, 1980

[54] THREE PHASE ANTIPERSPIRANT STICK

[75] Inventor: David L. Shelton, Cincinnati, Ohio

[73] Assignee: The Procter & Gamble Company, Cincinnati, Ohio

[21] Appl. No.: 924,478

[22] Filed: Jul. 13, 1978

Related U.S. Application Data

[63] Continuation-in-part of Ser. No. 883,075, Mar. 3, 1978, abandoned, which is a continuation-in-part of Ser. No. 817,075, Jul. 18, 1977, abandoned.

[51] Int. Cl.² ............................ A61K 7/34; A61K 7/38
[52] U.S. Cl. ................................ 424/66; 424/DIG. 5; 424/68; 424/362
[58] Field of Search ....................... 424/DIG. 5, 66, 68

[56] References Cited

U.S. PATENT DOCUMENTS

| | | | |
|---|---|---|---|
| 1,320,855 | 11/1919 | Henderson | 424/DIG. 5 |
| 1,984,669 | 12/1934 | Taub | 424/67 |
| 2,087,161 | 7/1937 | Moore | 424/67 |
| 2,087,162 | 7/1937 | Moore | 424/68 |
| 2,566,722 | 9/1951 | Friedberg | 424/64 |
| 2,732,327 | 1/1956 | Teller | 424/DIG. 5 |
| 2,900,306 | 8/1959 | Slater | 424/DIG. 5 |
| 2,933,433 | 4/1960 | Teller | 424/DIG. 5 |
| 2,970,083 | 1/1961 | Bell | 424/68 |
| 3,192,933 | 7/1965 | Prince | 424/DIG. 5 |
| 3,255,082 | 6/1966 | Barton | 424/DIG. 5 |
| 3,259,545 | 7/1966 | Teller | 424/DIG. 5 |
| 3,856,931 | 12/1974 | Fuchs et al. | 424/14 |
| 3,957,969 | 5/1976 | Fujuyama et al. | 424/64 |
| 4,049,792 | 9/1977 | Elsnau | 424/66 |
| 4,083,956 | 4/1978 | Shelton | 424/68 |
| 4,120,948 | 10/1978 | Shelton | 424/DIG. 5 |

OTHER PUBLICATIONS

Bennett, Industrial Waxes, vol. I, 1975, pp. Introduction, 156 to 171.
Teng, et al., Cosm. & Perfumery, 10/1975. vol. 90, pp. 32, 34, 36 & 42 & 43.

Primary Examiner—Dale R. Ore
Attorney, Agent, or Firm—Douglas C. Mohl; John V. Gorman; Richard C. Witte

[57] ABSTRACT

Stable, three-phase antiperspirant stick compositions having (1) a solid, shearable antiperspirant phase, (2) a gel phase comprising a polyhydric aliphatic alcohol gelled with soap, and (3) a barrier phase of specified minimum thickness separating the antiperspirant and gel phases comprising a water-insoluble, alcohol-insoluble, high melting point wax and liquid emollient and which is relatively free of particulate materials. Such antiperspirant sticks provide effective antiperspirant performance as well as desirable application characteristics.

13 Claims, 4 Drawing Figures

THREE PHASE ANTIPERSPIRANT STICK

CROSS REFERENCE TO RELATED APPLICATION

This application is a continuation-in-part of my co-pending application, Ser. No. 883,075, filed Mar. 3, 1978, which in turn is a continuation-in-part of application, Ser. No. 817,075, filed July 18, 1977 both are now abandoned.

BACKGROUND OF THE INVENTION

1. Field of the Invention

The present invention relates to antiperspirant compositions in the form of solid sticks. The compositions herein comprise three phases, one of which is an antiperspirant phase containing antiperspirant materials, a second of which is an alcohol gel phase which can contain deodorant materials and a third of which is a barrier phase isolating and insulating the other two phases from each other.

2. The Prior Art

Antiperspirant compositions in stick form are known in the art. Single phase antiperspirant compositions have, for example, been disclosed in Taub; U.S. Pat. No. 1,984,669; issued Dec. 18, 1934 and Procter & Gamble; British Pat. No. 1,433,695; granted Aug. 25, 1976. Stick compositions of this type typically employ large amounts of waxy materials as the vehicle which delivers the antiperspirant active to the skin. The antiperspirant active materials often are present in the stick in particulate form which is particularly effective. Such stick products are stable and are especially effective for delivering large amounts of antiperspirant salts to the skin.

Attempts have been made to realize deodorant and antiperspirant sticks which deliver active ingredients to the skin via a vehicle which glides easily over the skin surface and which imparts a cooling sensation to the skin both during and after application. Soap/alcohol gels can provide such cosmetic benefits. However, incorporation of conventional astringent antiperspirant salts into such gels tends to interfere with the gel structure and render it less cosmetically desirable. To solve such compatibility problems, soap/alcohol gel sticks have been formulated using special additives such as lactate salts. (See, for example, Teller; U.S. Pat. No. 2,732,327, issued Jan. 24, 1956 and Slater; U.S. Pat. No. 2,900,306, issued Aug. 18, 1959). Some soap/alcohol gel antiperspirant sticks have also been formulated in two phases with an inner core containing gel-compatible antiperspirant salts and an outer shell containing deodorant materials (See Bell, U.S. Pat. No. 2,970,083, issued Jan. 31, 1961).

Combinations of a conventional waxy antiperspirant composition with a soap/alcohol gel to form a two-phase stick composition could enhance composition efficacy and improve composition cosmetic benefits. Such combination is, however, not made without certain difficulties. While each phase alone of such a stick composition is stable, contact between the two phases can cause destructive interaction between the two phases. The alcohol/gel phase experiences syneresis which is a bleeding or leaking of the gelled alcohol from the gel structure or matrix. Such leaked alcohol can interact with components of the waxy phase and can thus consume or physically separate the phases, thereby resulting in an unacceptable consumer product.

It is speculated herein that this problem of interfacial interaction is due to, or at least exacerbated by, the presence of particulate materials in the antiperspirant phase. Often, the particulate material present in the antiperspirant phase is the antiperspirant active material itself. The particulate may be present, however, merely as a filler or inert component. The ability of the barrier phase to affect gel pH is also a factor in product stability.

Given the state of the antiperspirant art as described above, there is a continuing need for new and useful antiperspirant stick compositions which are stable and which provide both good antiperspirant efficacy as well as desirable application characteristics. Accordingly, it is an object of the present invention to provide multi-phase antiperspirant sticks with effective antiperspirancy performance and desirable application characteristics.

It is a further object of the present invention to provide multi-phase antiperspirant sticks which are dimensionally stable.

It is a further object of the present invention to provide such multi-phase antiperspirant sticks which do not exhibit severe interfacial interaction.

It is a further object of the present invention to provide multi-phase antiperspirant sticks which can deliver both antiperspirant and deodorant materials to the skin simultaneously.

It has been surprisingly discovered that the above objectives can be realized and superior multi-phase antiperspirant sticks provided by formulating a stick having a thin waxy barrier of specific composition and which is relatively free of particulate materials and has an appropriate pH. This third barrier phase prevents interfacial interaction when present in the region interjacent to a solid shearable antiperspirant phase which preferably utilizes particular amounts of certain types of waxes, emollients and particulate antiperspirant actives and a gel phase formulated with particular amounts of certain polyhydric alcohols and gel-forming agents.

SUMMARY OF THE INVENTION

The present invention relates to antiperspirant compositions in the form of a three-phase stick. Such compositions comprise from about 35% to 65% by weight of a shearable, solid antiperspirant phase, from about 35% to 65% by weight of a gel phase; and an interjacent barrier phase contiguous to both the gel and the antiperspirant phase, which barrier phase comprises from about 1% to 10% by weight of the total antiperspirant composition.

The antiperspirant phase of the three-phase stick compositions can be any solid, shearable material which can deliver an astringent antiperspirant active. Preferably, the antiperspirant phase contains from about 2% to 15% by weight of the antiperspirant phase of a high melting point wax, from about 20% to 50% by weight of the antiperspirant phase of a water-insoluble, liquid, organic emollient and from about 15% to 60% by weight of the antiperspirant phase of particulate astringent antiperspirant material on an anhydrous basis. The high melting point wax utilized in the antiperspirant phase has a melting point between about 150° F. and 215° F.

The gel phase of the three-phase stick compositions contains from about 10% to 92% by weight of gel phase of a polyhydric alcohol and from about 5% to 15% by weight of gel phase of a gel forming agent.

The polyhydric alcohol used in the gel phase can be a polyhydric aliphatic alcohol having from 2 to 3 carbon atoms and 2 or 3 hydroxyl groups. The gel forming agent can be either a sodium or potassium salt of a fatty acid having from 14 to 18 carbon atoms.

The barrier phase of the three-phase sticks herein has a thickness of at least about 0.005 inch. This barrier phase comprises from about 10% to 40% by weight of the barrier phase of a water-insoluble, alcohol-insoluble, high melting point wax and from about 20% to 90% of a liquid organic emollient. The barrier phase should be relatively free of particulate materials and not be capable of lowering the gel pH below about 9.5.

Preferred embodiments of the three-phase stick compositions herein provide the antiperspirant phase in the form of a core, the barrier phase in the form of a tubular sleeve interjacent, and with the gel phase surrounding the sleeve forming a shell. Preferred embodiments also include three-phase sticks wherein the gel phase contains a monohydric alcohol component to provide a skin cooling sensation and a deodorant material to provide deodorant efficacy.

DETAILED DESCRIPTION OF THE INVENTION

Figure 1:
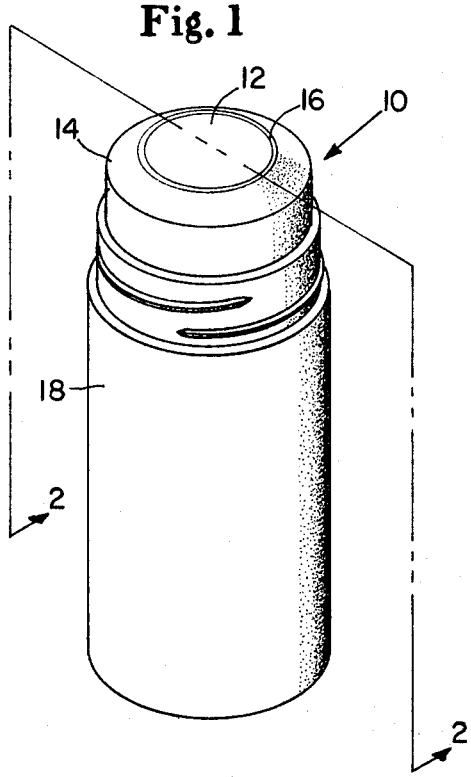
FIG. 1 is a perspective view of the preferred embodiment of the present invention with the cosmetic portion partially extended.

The three-phase antiperspirant stick compositions of the present invention comprise (A) an antiperspirant phase, (B) a gel phase and (C) an interjacent barrier phase contiguous to both the antiperspirant and gel phases. These essential elements as well as optional components, composition preparation, and composition use are discussed in detail as follows:

ANTIPERSPIRANT PHASE

One essential component of the antiperspirant sticks herein is a solid, shearable phase. This phase provides the vehicle for the antiperspirant-active ingredient. Such an antiperspirant phase generally serves to deliver antiperspirant material(s) to the skin via a medium which does not feel runny, cold, or sticky. The antiperspirant phase component of the stick compositions herein comprises from about 35% to 65%, preferably from about 45% to 55%, by weight of the total composition. The antiperspirant phase is solid (i.e., able to retain a rigid form at 20° C.) and is shearable (i.e., yields easily when rubbed onto the skin in the normal manner of usage of cosmetic sticks.)

Many solid antiperspirant compositions are known in the art which tend to interact with soap/alcohol gels if such antiperspirant compositions are formulated into stick products along with such soap/alcohol gels. It has been discovered, however, that such antiperspirant compositions can be combined with soap/alcohol gels in the three-phase stick products of the present invention.

The skilled artisan can readily formulate a large number of solid compositions which have antiperspirant effectiveness and have shearable cosmetics and which are thus suitable for use as the antiperspirant phase of the stick compositions herein.

In an especially preferred embodiment, the antiperspirant phase is substantially anhydrous, (i.e., comprises no more than about 1.0% by weight of the antiperspirant phase of water in addition to the waters of hydration on the antiperspirant salt), provides the antiperspirant active in an especially effective undissolved particulate form, and comprises a water-insoluble wax, a liquid organic emollient and particulate antiperspirant-active material.

Water-Insoluble Wax

A high melting point, water-insoluble wax is the principal component of the antiperspirant phase in a preferred embodiment of the stick compositions herein. It is believed that the high melting point wax provides a structure which can be sheared during application to the skin, thereby depositing layers of wax and antiperspirant active particles onto the skin.

The antiperspirant phase herein contains from about 2% to 15%, preferably from about 3% to 11%, by weight of antiperspirant phase of the water-insoluble wax materials. Maintenance of wax concentrations within these limits permits the realization of acceptable stick cosmetic characteristics. Furthermore, exposure to normal temperature extremes, especially during summer, might deform sticks without high melting point wax concentrations within the limits indicated.

The waxes employed as an essential component of the preferred antiperspirant phase of the sticks herein are essentially water-insoluble (soluble to an extent of less than 0.5% by weight in water at 80° F.). Such waxes have a melting point within the range of from about 150° F. to about 215° F., preferably within the range of from about 170° F. to 210° F. Such waxes are referred to as high melting point waxes. Examples of suitable high melting point waxes are beeswax, carnauba, bayberry, candelilla, montan, ozokerite, ceresin, paraffin, synthetic waxes such as Fisher-Tropsch waxes, and microcrystalline wax. Preferred high melting point waxes are ceresin, ozokerite, white beeswax and synthetic waxes. It is understood that mixtures of the high melting point waxes are acceptable for use in the compositions herein.

Liquid Organic Emollient

A second essential component of the preferred antiperspirant phase is a liquid organic emollient. The emollient component serves to improve the cosmetic acceptability of the compositions herein by helping to impart a soft, supple character to the skin treated with the instant stick compositions.

The emollients used herein can be any non-toxic, organic material or mixtures thereof which is of low irritation potential, which is liquid at 20° C. and which is substantially water-insoluble (i.e. water solubility of from about 0.5% to 1.0% by weight in water at 20° C.). However, the liquid emollients of this invention are water-dispersible in the presence of a surfactant, e.g., soap, which is desirable in that it permits the removal of the composition during washing or bathing. The emollient component comprises from about 20% to 50%, preferably from about 30% to 40%, by weight of the antiperspirant phase.

Suitable organic emollients include fatty acid and fatty alcohol esters and water insoluble ethers. Examples of such emollients include isopropyl myristate, isopropyl palmitate, cetyl acetate, cetyl propionate, di-n-butyl phthalate, diethyl sebacate, diisopropyl adipate, ethyl carbomethyl phthalate, and the condensation product of about 14 moles of propylene oxide with one mole of butyl alcohol (Fluid AP ®). Preferred organic liquid emollients include isopropyl myristate, isopropyl palmitate, di-n-butyl phthalate, and Fluid AP ®. Especially preferred organic emollients include isopropyl myristate, isopropyl palmitate and Fluid AP ®.

Suitable emollients for use herein also include both volatile and non-volatile polyorganosiloxane materials. Useful alcohol-soluble materials of this type can have the chemical structure:

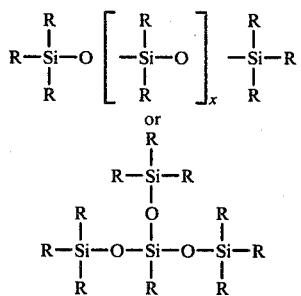

wherein the R groups can be the same or different and are selected from $C_1$-$C_4$ alkyl groups and phenyl groups, wherein x equals the number of repeating diorganosiloxy groups and wherein the viscosity of said organopolysiloxane is from about 9 to about 50 cs at 25° C. Examples of such organopolysiloxanes include DC-556 fluid, which is tris (trimethylsiloxy) phenylsilane and DC-225 fluid, a polydimethylsiloxane having a viscosity of 9.5 cs at 25° C., both marketed by Dow Corning Corporation. Preferred polysiloxane emollients include SWS-03314 marketed by Stauffer Chemical Company and UC-7158 or UC-7207 each marketed by Union Carbide Corporation.

Emollients including the liquid emollients suitable for use herein are described more fully in Balsam and Sagarin, *Cosmetics Science and Technology*, 2nd. Ed., Vol. 1, Wiley-Interscience, 1972, Chapter 2, pp. 27–104 and in U.S. Pat. No. 4,045,548, Aug. 30, 1977 to Luedders et al. Both are incorporated herein by reference.

Particulate Antiperspirant Material

A third essential component of the preferred antiperspirant phase of the present compositions comprises a particulate astringent antiperspirant material. Such antiperspirant active material, of course, imparts antiperspirancy efficacy to the antiperspirant stick compositions of the present invention.

Any aluminum astringent antiperspirant salt or aluminum and/or zirconium astringent complex in particulate form can be employed herein. Such salts and complexes are well known in the antiperspirant art. Salts useful as astringent antiperspirant salts or as components of astringent complexes include aluminum halides, aluminum hydroxyhalides, zirconyl oxyhalides, zirconyl hydroxyhalides and mixtures of these salt materials.

Aluminum salts of this type include aluminum chloride and the aluminum hydroxyhalides having the general formula $Al_2(OH)_xQ_y \cdot XH_2O$ where Q is chlorine, bromine or iodine; where x is 2 to 5 and $x+y=6$ and x and y do not need to be integers; and where X is about 1 to 6. Aluminum salts of this type can be prepared in the manner described more fully in Gilman, U.S. Pat. No. 3,887,692, issued June 3, 1975, incorporated herein by reference.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein z may vary from about 0.9 to 2 and need not be an integer, n is the valence of B, 2-nz is greater than or equal to 0, and B may be selected from the group consisting of halides, nitrate, sulfamate, sulfate and mixtures thereof. Although only zirconium compounds are exemplified in this specification, it will be understood that other Groups IV B metals, including hafnium could be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amount of the hydroxyl group, varying from about 1.1 to only slightly greater than 0 groups per molecule.

Several types of antiperspirant complexes utilizing the above antiperspirant salts are known in the art. For example, Luedders et al; U.S. Pat. No. 3,792,068, issued February 12, 1974 discloses complexes of aluminum, zirconium and amino acids such as glycine. Complexes such as those disclosed in this Luedders et al '068 patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to 12.5 and a Metal:Cl ratio of from about 0.73 to 1.93.

Preferred ZAG complexes are formed by
(A) Co-dissolving in water
  (1) one part $Al_2(OH)_{6-m}Q_m$, wherein Q is an anion selected from the group consisting of chloride, bromide and iodide and m is a number from about 0.8 to about 2.0;
  (2) x parts $ZrO(OH)_{2-a}Q_a \cdot nH_2O$ where Q is chloride, bromide or iodide; where a is from 1 to 2; where n is from 1 to 8; and where x has a value of from about 0.16 to about 1.2;
  (3) p parts neutral amino acid selected from the group consisting of glycine, dl-tryptophane, dl-β-phenylalanine, dl-valine, dl-methionine and β-alanine, and where p has a value of from about 0.06 to about 0.53;
(B) Co-drying the resultant mixture to a friable solid; and
(C) Reducing the resultant dried inorganic-organic antiperspirant complex to particulate form.

The preferred aluminum compound for preparation of such ZAG type complexes is aluminum chlorhydroxide of the empirical formula $Al_2(OH)_5Cl.2H_2O$. The preferred zirconium compounds for preparation of such ZAG-type complexes are zirconyl hydroxychloride having the empirical formula $ZrO(OH)Cl.3H_2O$ and the zirconyl hydroxyhalides of the empirical formula $ZrO(OH)_{2-a}Cl_a.nH_2O$ wherein a is from 1.5 to 1.87 and n is from about 1 to 7. The preferred amino acid for preparing such ZAG-type complexes is glycine of the formula $CH_2(NH_2)COOH$. (Salts of such amino acids can also be employed in such antiperspirant complexes. See U.S. Pat. No. 4,017,599 to A. M. Rubino issued Apr. 12, 1977 specifically incorporated herein by reference.)

A wide variety of other types of antiperspirant complexes are also known in the art. For example, Siegal; U.S. Pat. No. 3,903,258, issued Sept. 2, 1975 discloses a zirconium aluminum complex prepared by reacting zirconyl chloride with aluminum hydroxide and aluminum chlorhydroxide. Rubino; U.S. Pat. No. 3,979,510, issued Sept. 7, 1976 discloses an antiperspirant complex formed from certain aluminum compounds, certain zirconium compounds and certain complex aluminum buffers. Rubino; U.S. Pat. No. 3,981,896, issued Sept. 21, 1976 discloses an antiperspirant complex prepared from an aluminum polyol compound, a zirconium compound and an organic buffer. Mecca; U.S. Pat. No. 3,970,748, issued July 20, 1976 discloses an aluminum chlorhydroxy glycinate complex of the approximate general formula $[Al_2(OH_4)Cl][H_2CNH_2COOH]$. All of these patents are incorporated herein by reference.

Of all the above types of antiperspirant actives, preferred compounds include the 5/6 basic aluminum salts of the empirical formula $Al_2(OH)_5Cl.2H_2O$; mixtures of $AlCl_3.6H_2O$ and $Al_2(OH)_5Cl.2H_2O$ with aluminum chloride to aluminum hydroxychloride weight ratios of up to about 0.5; ZAG type complexes wherein the zirconium salt is $ZrO(OH)Cl.3H_2O$; the aluminum salt is $Al_2(OH)_5Cl.2H_2O$; and the amino acid is glycine and ZAG-type complexes wherein the zirconium salt is $ZrO(OH)_{2-a}Cl_a.nH_2O$ with a ranging from about 1.5 to 1.87 and n ranging from about 1 to 7; the aluminum salt is $Al_2(OH)_5Cl.2H_2O$; and the amino acid is glycine.

The preferred embodiment of the antiperspirant phase of the present stick compositions contains from about 11% to 50%, preferably from about 30% to 46%, by weight of the antiperspirant phase of the particulate astringent antiperspirant materials calculated on an anhydrous metal salt basis (exclusive of glycine, the salts of glycine or other complexing agents). Such particulate antiperspirant material is preferably impalpable, i.e. has particle sizes ranging from about 1 to about 100 microns, more preferably from about 1 to about 50 microns. The antiperspirant active material herein is preferably alcohol insoluble.

Optional Antiperspirant Phase Components

The antiperspirant phase of the instant stick compositions can contain a variety of optional ingredients suitable for improving composition efficacy, stability, cosmetics and/or aesthetics. Such optional antiperspirant phase components include low melting point waxes to adjust stick cosmetics, inert filler material to improve composition stability and cosmetics, perfumes, dyes, coloring agents, preservatives and the like.

A highly preferred optional component of the preferred antiperspirant phase is an additional wax material having a melting point of from about 100° F. up to 150° F. Such optional waxes are referred to herein as low melting point waxes. The low melting point wax component can be used as an adjunct to the high melting point wax to provide improved emolliency and to enhance the structural integrity of the waxy antiperspirant phase. The low melting point wax can also be used to adjust the feel of the stick compositions herein. One skilled in the art will easily be able to make a product which feels more brittle, soft, slippery, sticky, rough, etc., by blending various suitable low melting point waxes with the essentially present high melting point waxes.

Examples of useful low melting point waxes include fatty acids containing from about 12 to 20 carbon atoms, fatty alcohols containing from about 12 to 20 carbon atoms, silicone waxes and glycerol monostearate. Especially preferred materials of this type are the $C_{12}$ to $C_{20}$ fatty acids and $C_{12}$ to $C_{20}$ fatty alcohols. The most preferred low melting point waxes are cetyl alcohol, stearyl alcohol, myristyl alcohol, lauryl alcohol and glycerol monostearate.

If present, the low melting point wax, or mixtures thereof, component generally comprises from about 2% to 20%, more preferably from about 5% to 15%, by weight of the antiperspirant phase.

Another preferred optional component for possible use in the antiperspirant phase of the stick compositions herein is an inert filler material. Such filler materials also serve to enhance the structural integrity of the antiperspirant phase herein and serve to improve composition cosmetics.

Useful inert particulate filler materials include talc; colloidal silica, e.g., Cab-O-Sil (Cabot Corp.), a pyrogenic silica having an average particulate diameter between about 0.01 and 0.3 microns as disclosed in British patent No. 987,301 and British Patent No. 1,167,173, and finely divided hydrophobic clays such as the reaction product of a clay such as bentonite and dimethyldistearyl ammonium chloride, such treated clays being marketed under the tradename "BENTONE" by NL Industries. Such clay materials are described more fully in British Patent No. 1,167,173.

If present, the inert particulate filler material generally comprises from about 0.5% to 5.0% by weight of the waxy antiperspirant phase of the present stick compositions.

The antiperspirant phase herein can also contain minor amounts i.e., from about 0.1% to 1.5% by weight of antiperspirant phase, of conventional additives such as dyes, perfumes, pigments, coloring agents, etc. In selecting such ingredients only small amounts of hydrophilic materials shall be used in addition to the active material. Preferably, less than about 5% of the antiperspirant phase, in addition to the antiperspirant materials, is soluble in water.

GEL PHASE

The second essential component of the antiperspirant sticks of this invention is a gel phase formed from certain polyhydric aliphatic alcohols and certain gel-forming agents. This gel phase comprises from about 35% to 65%, preferably from about 45% to 55%, by weight of the total antiperspirant stick compositions herein. The primary purpose of the gel phase of the sticks herein is to improve the glidability and ease of application of the instant stick compositions onto the skin. Optionally, the gel phase herein can also act as a carrier for deodorant materials and for materials such as monohydric alcohols which impart a desirable cooling, moist sensation to the skin upon application.

Polyhydric Aliphatic Alcohol

One essential component of the gel phase of the present antiperspirant stick compositions is a polyhydric aliphatic alcohol containing 2 or 3 carbon atoms and from 2 to 3 hydroxyl groups. This polyhydric alcohol or mixtures thereof is the medium which is "gelled" to form the gel phase of the stick compositions herein. The polyhydric aliphatic alcohol component of the gel phase comprises from about 10% to 92%, preferably from about 15% to 50%, by weight of the gel phase.

Suitable polyhydric alcohols for use in the gel phase herein include ethylene glycol, propylene glycol, trimethylene glycol, and glycerine. The most preferred polyol is propylene glycol.

Gel Forming Agents

The second essential component of the gel phase of the antiperspirant stick compositions herein is a gel forming agent which is added to the polyhydric aliphatic alcohol of the gel phase to form the desired gel material. The gel forming agents used herein can be the sodium and potassium salts (i.e. soaps) of fatty acids containing from about 14 to 18 carbon atoms.

Gel forming agents generally comprise from about 5% to 15% by weight of the gel phase herein, preferably from about 7% to 10% by weight of the gel phase. If the gel forming agent concentrations lower than those specified are employed, the gels formed tend to be dimensionally unstable and tend to deform at summertime temperatures. If concentrations of gel forming agents above those specified are utilized, the gels formed tend to be too hard and do not exhibit desirable glide and application characteristics. By utilizing gel-forming agents of the particular type described and in the concentrations specified, gel phases can be formulated which exhibit structural integrity and which exhibit cosmetically desirable application properties.

The fatty acid portion of the soap gel forming agents should be essentially pure saturated or unsaturated higher fatty acids having a $C_{14}$ to $C_{18}$ backbone. Suitable mixtures of such acids can be employed provided that such mixtures are free from significant proportions of other fatty acids of higher or lower chain length which substantially adversely affect or neutralize the desired gel forming effects.

Examples of fatty acids useful in synthesizing the gel forming agents herein include myristic, palmitic, stearic, oleic, linoleic, linolenic, behenic, margaric acids and the mixtures of such acids. Naturally occurring sources of such fatty acids include coconut oil, beef tallow, lanolin, fish oil, beeswax, palm oil, peanut oil, olive oil, cottonseed oil, soybean oil, corn oil, rapeseed oil, rosin acids, and greases. Conventional fractionation and/or hydrolysis techniques can be employed if necessary to obtain the requisite types of fatty acids from such materials.

Preferred fatty acid soap type gel forming agents include sodium stearate, sodium palmitate, potassium stearate, potassium palmitate and sodium myristate. The most preferred gel forming agent is sodium stearate.

Optional Gel-Phase Components

The gel phase of the instant stick compositions can contain a variety of optional ingredients suitable for improving composition efficacy, stability, cosmetics and/or aesthetics. Such optional gel phase components include monohydric alcohols to improve composition cosmetics, water in small amounts, deodorant materials, alcohol evaporation retardants, and anti-syneresis agents, perfumes, dyes, pigments, coloring agents and the like.

A highly preferred optional component of the gel phase is a monohydric alcohol which serves to impart a cosmetically desirable cooling sensation to the skin. Monohydric alcohols of this type contain one to three carbon atoms. Examples of suitable monohydric alcohols include methanol, ethanol, isopropanol, and n-propanol. Preferred monohydric alcohols are ethanol and isopropanol.

While monohydric alcohols can provide a desirable cosmetic cooling benefit for the antiperspirant stick compositions herein, inclusion of a monohydric alcohol component can also lead to stick composition instability problems. Monohydric alcohols tend to produce dimensional instability of the gel phase and tend to cause the gel phase to evaporate and thereby become sticky as well as to deteriorate and assume a dried and shriveled appearance.

It has been surprisingly discovered that such problems can be minimized and that monohydric alcohols can be successfully incorporated into the gel phase of the stick compositions herein provided certain concentration limits for the essential gel phase components are observed. When monohydric alcohols are employed, it has been found that the weight ratio of polyhydric alcohol to gel forming agent must exceed about 2.45. When polyhydric aliphatic alcohols and gel forming agents are present in this ratio, monohydric alcohols can be incorporated into the gel phase in amounts of from about 10% to 72%, preferably from about 40% to 70%, by weight of the gel phase.

When monohydric alcohols are employed, another highly preferred optional component of the gel phase is a material which helps retard alcohol evaporation and which acts as an anti-syneresis agent. Especially preferred materials of this type are cellulose derivatives such as hydroxyalkylcelluloses. Especially preferred materials of this type are hydroxypropylcellulose compounds having the chemical formula:

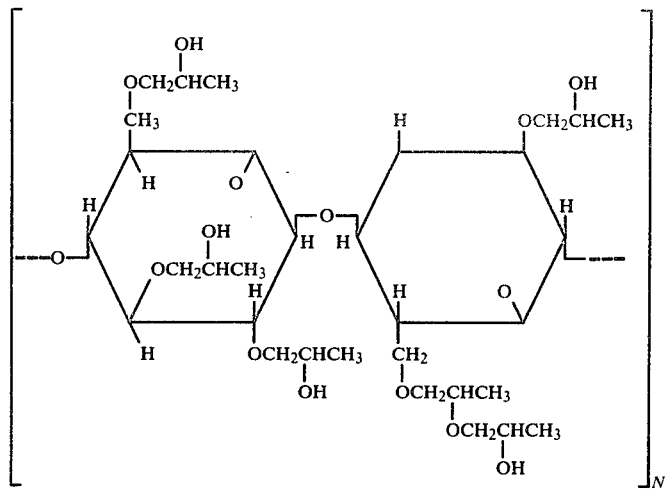

and wherein N is sufficiently large such that the total molecular weight of the material ranges from about 60,000 to 1,000,000. Such materials are sold under the tradename of Klucel ® by Hercules Incorporated. If present, such alcohol evaporation retarding agents and anti-syneresis agents comprise from about 0.1% to 5.0% by weight of the gel phase.

Another optional ingredient of the gel phase herein is a conventional deodorant material. Suitable deodorants include bacteriostatic quaternary ammonium compounds such as cetyltrimethylammonium bromide, cetyl pyridinium chloride, benzethonium chloride, diisobutyl phenoxy ethoxy ethyl dimethyl benzyl ammonium chloride, N-alkylpyridinium chloride, N-cetyl pyridinium bromide, sodium N-lauroyl sarcosine, sodium N-palmetoyl sarcosine, lauroyl sarcosine, N-hyristoyl glycine, potassium N-lauroyl sarcosine and stearyl trimethyl ammonium chloride. If present, deodorants generally comprise from about 0.1% to 1.0% by weight of the gel phase.

Conventional optional ingredients such as perfumes, dyes, pigments, coloring agents and the like can also be added to the gel phase. If present such minor additions comprise from about 0.1% to 1.5% by weight of the gel phase.

Small amounts of water can be added to the gel phase. The amount of water added should, however, be limited to less than about 10%. Water can be used as a solvent for an optional dry material or for an optional deodorant material. Water in the gel phase at concentrations exceeding 10% tends to produce a gel phase which is undesirably soft.

BARRIER PHASE

The third essential component of the antiperspirant sticks of this invention is the barrier phase. The barrier phase serves to segregate the gel phase from the antiperspirant phase and thereby effectively eliminates the problem of destructive interfacial interaction. The barrier phase comprises from about 1% to 10%, preferably about 2% to 4% by weight of the total antiperspirant stick compositions herein. To insure that the barrier phase constitutes a continuous layer of protection, the barrier phase should have a minimum thickness of at least about 0.005 of an inch. Preferably, the barrier phase ranges in thickness from about 0.010 inch to 0.040 inch.

It has been found that when certain formulations of the gel phase and the antiperspirant phase (such as the preferred embodiment herein) are in physical contact, a destructive interfacial interaction occurs. This phenomenon of interfacial interaction involves the alcohol(s) escaping from the gel structure and migrating into the antiperspirant core phase where the emollient is solubilized by the alcohol(s). It is speculated that when the gel phase and the chemically dissimilar antiperspirant phases are in juxtaposition then the polyhydric and monohydric alcohols, antiperspirant active, and emollient concentration gradients create a diffusional driving force which causes the polyhydric alcohol to migrate from the gel phase into the antiperspirant phase. Conversely, dissolved antiperspirant material and the emollients tend to migrate from the antiperspirant phase into the gel phase. The gross effect is an antiperspirant phase plasticization and, ultimately, a noticeable liquid runoff and a concommittant shrinking of both the gel phase and the antiperspirant phase. The liquid runoff also tends to undesirably plasticize the antiperspirant phase. While such theoretical interpretation does not limit the scope of this invention, it is believed that the particulate antiperspirant material in the antiperspirant phase provides diffusion pathways for the alcohol of the gel phase to migrate into the adjacent antiperspirant phase.

It has been surprisingly discovered that a thin wax/emollient barrier in the region interjacent to the gel phase and the antiperspirant phase effectively prevents this interfacial interaction. Such a wax/emollient barrier must be relatively free (i.e. present to an extent of less than about 5% by weight of the barrier phase) of the particulate material (i.e. discreet solid material having a particle size of greater than about one micron). It is speculated that by providing a region of waxy material which is relatively free of the diffusion pathways provided by particulate materials, the migration of the alcohol into the antiperspirant phase is effectively prevented. Effectively isolated by the interjacent, alcohol-impermeable barrier phase, the gel phase and antiperspirant phase of the three-phase sticks exhibit negligible destructive interfacial interaction.

The barrier phase of the compositions herein should also be free of materials capable of lowering the pH of the gel phase substantially. The barrier should preferably not contain materials capable of lowering the gel pH in the area of the gel/barrier interface below about 9.5 (pH's below this value tend to deleteriously affect the integrity of the gel phase). Gel pH can be determined at anytime/temperature. Determination of deleterious gel defects as a result of acidic material in the barrier can best be determined after the product has been stored for one week at 120° F.

The barrier phase embodiments of the present invention provide the further advantage of having shear rates roughly comparable to both the gel and the antiperspirant phases herein. Thus, the barrier phase when applied to the skin wears away at approximately the same rate as the gel phase and the antiperspirant phase. Undesirable phase protrusion that would occur were one phase worn away more slowly is thereby avoided. Additionally, the barrier phases of the present invention provide the additional cosmetic advantage of being visually unnoticeable. The skilled artisan can easily formulate barrier phases and antiperspirant phases which have no readily apparent boundary.

The two essential components of barrier phases herein are alcohol-insoluble waxes and liquid organic emollients.

Alcohol—Insoluble Waxes

An essential component of the barrier phase of the present antiperspirant stick compositions is a high melting point, water-insoluble wax or mixtures thereof which is insoluble in the polyhydric alcohol or mixtures thereof which are present in the gel phase (i.e. alcohol solubility of less than 1% at 80° F.) Such waxes are a subgroup of those waxes suitable as the principal component of the preferred antiperspirant phase of the stick compositions herein. Generally such waxes are non-polar compounds such as hydrocarbon waxes. Suitable waxes have a melting point within the range of from about 150° F. to 215° F., preferably within the range of from about 170° F. to 210° F. Examples of suitable waxes are ozokerite, paraffin, and ceresin.

The barrier phase herein contains from about 10% to 40%, preferably from about 20% to 40%, by weight of the barrier phase of the alcohol-insoluble wax. The skilled artisan will recognize that barrier phases containing higher levels of the alcohol-insoluble wax will have less desirable cosmetic characteristics. The skilled artisan may then wish to adjust the maximum thickness of barrier phases having higher wax concentrations so as to alleviate the perception of toughness.

Liquid Organic Emollient

A second essential component of the barrier phase is a liquid organic emollient. This liquid emollient component serves to improve the cosmetic acceptability of the barrier phase herein in the same manner as the emollient component of the antiperspirant phase. The emollients suitable for use in the barrier phase herein are the same as are used in the antiperspirant phase as described above. The emollient component comprises from about 20% to 90% by weight of the barrier phase.

Optional Barrier Phase Components

The barrier phase of the instant stick compositions can contain a variety of optional ingredients suitable for improving composition stability, cosmetics or aesthetics so long as the barrier phase is relatively free of discreet particulate material and does not contain undesirable acidic materials. Such optional barrier phase components include low melting point waxes to adjust stick cosmetics, perfumes, dyes, preservatives and the like.

As noted, a highly preferred optional component of the barrier phase is an additional low-melting wax material or mixtures thereof having a melting point of from about 100° F. up to 150° F. Such optional waxes are referred to herein as low melting point waxes. The low melting point wax component can be used as an adjunct to the high melting point wax to provide improved emolliency and to enhance the structural integrity of the barrier phase. The low melting point wax can also be used to adjust the feel of the stick compositions herein. One skilled in the art will easily be able to make a product which feels more brittle, soft, slippery, sticky, rough, etc., by blending various suitable low melting point waxes with the essentially present high melting point waxes.

Examples of useful low melting point waxes include fatty acids containing from about 12 to 20 carbon atoms, fatty alcohols containing from about 12 to about 20 carbon atoms, silicone waxes and glycerol monostearate. Especially preferred materials of this type are the $C_{12}$ to $C_{20}$ fatty acids and $C_{12}$ to $C_{20}$ fatty alcohols. The most preferred low melting point waxes are cetyl alcohol, stearyl alcohol, myristyl alcohol, lauryl alcohol and glycerol monostearate.

If present, the low melting point wax component generally comprises from about 5% to 50%, and preferably from about 10% to 20% by weight of the barrier phase.

The barrier phase herein can also contain conventional additives such as dyes, perfumes, preservatives, deodorants, etc. If present, such materials should constitute a minor portion of the barrier phase, i.e., from about 0.1% to 1.5% by weight of the barrier phase.

COMPOSITION PREPARATION

The antiperspirant, gel and barrier phases of the present stick compositions are prepared separately. The preferred waxy antiperspirant phase of the present compositions is generally prepared by heating the solid wax and liquid emollient in a suitable container while gently stirring. When the wax or waxes are melted and mixed thoroughly with the emollient, the antiperspirant-active ingredient is mixed and dispersed in the melt. The optional ingredients can then be added or the melt can be cooled to a temperature above the solidification point before adding additional ingredients. The barrier phase of the present composition is generally prepared in the same manner as the antiperspirant phase except that no particulate antiperspirant-active ingredient is added. Care should be taken in preparing the preferred antiperspirant phases herein and the barrier phase to avoid use of any materials or procedures which might introduce free moisture into the composition above the substantially anhydrous level.

The gel phase of the present composition can be prepared by admixing the essential and optional gel phase components together in such a manner as to produce a thickened, stable gel. In a preferred mode of gel preparation, the polyhydric aliphatic alcohol and the monohydric alcohol are mixed together in a reflux vessel with moderate agitation. Upon heating the mixture to boiling, the gel-forming agents can be added under continuing refluxing and agitation until the gel-forming agent fully dissolves. Optional ingredients such as dyes, deodorants and perfumes can then be added. Refluxing and moderate agitation is continued until boiling reoccurs if there has been an appreciable temperature drop due to the addition of the optional materials. The molten mixture can then be placed in a mold device such that the mixture is allowed to gel into a dimensionally stable mass of the desired geometric configuration.

Once prepared, the waxy antiperspirant, gel and barrier phases of the compositions herein can be joined or combined by any suitable means or in any suitable device so that a single antiperspirant stick is formed. In the stick product, the waxy antiperspirant and gel phases should be separated and isolated from each other by the interjacent barrier phase. The orientation of the phases should be such that all three phases are exposed in a single application surface.

Figure 2:
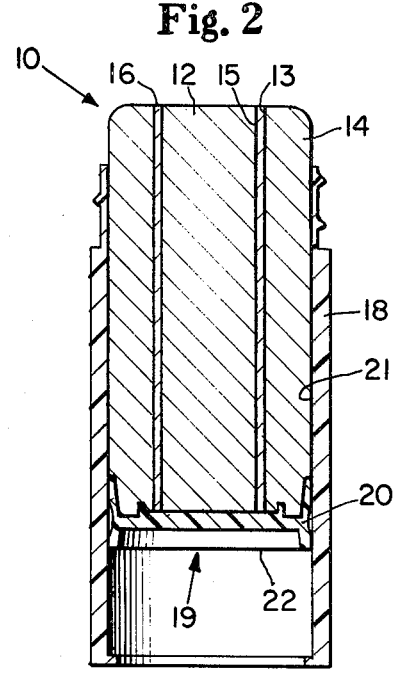
FIG. 2 is a cross-section taken on the line 2—2 of FIG. 1 with the thickness of the barrier phase exaggerated for clarity of illustration.

Referring now to the drawing, particularly to FIGS. 1 and 2 thereof, there is shown a preferred geometrical embodiment of the present invention. The waxy antiperspirant phase is formed as a core 12 of any suitable shape, the barrier phase is formed as a sleeve 16 surrounding the waxy antiperspirant phase or core 12 and the gel phase is formed as a shell 14 surrounding the barrier phase or sleeve 16. Most preferably, the antiperspirant core 12, the barrier phase sleeve 16, and the gel phase shell 14 are in the form of concentric cylinders.

The three-phase cylindrical stick compositions also possess a unique and appealing visual aesthetic quality. Generally, the antiperspirant core phase and barrier phase are each both opaque and white while the gel phase shell is translucent or even transparent. The juxtaposition of a white, opaque core and an encircling translucent gel phase—particularly when colored, e.g., blue—brings to mind a "bull's-eye" and, hence, these three-phase cylindrical sticks can be characterized as "bull's-eye" antiperspirant sticks.

To prepare three-phase cylindrical "bull's-eye" antiperspirant stick compositions of this type, the molten antiperspirant phase mixture is poured into a cylindrical mold and allowed to set. After reaching room temperature (75° F.) the antiperspirant phase core is removed from the mold. Thereafter, the core is dipped momentarily into the molten barrier phase mixture. Upon withdrawal from molten barrier phase mixture, the barrier coated core is again allowed to reach room temperature. The piece is then centered into another mold whose inner diameter is the desired stick diameter. The molten gel phase which can contain colorants is then added to the annular space and allowed to cool. Upon cooling, the three-phase "bull's-eye" sticks of the present invention are removed from the mold.

Referring again to the drawing, particularly to FIG. 2, the prepared antiperspirant stick 10 is carried by a moveable, inner piston 20 to define a stick/piston piece 19. The piston 20 is housed within the hollow cylinder 18. The tolerance between the stick-piston piece 19 and the interior wall 21 of the cylinder 18 is such that the stick/piston piece 19 can be manually pressed upward by exerting force on the piston's anterior face 22 to expose the distal end portion of antiperspirant stick 10 for use.

Figure 3:
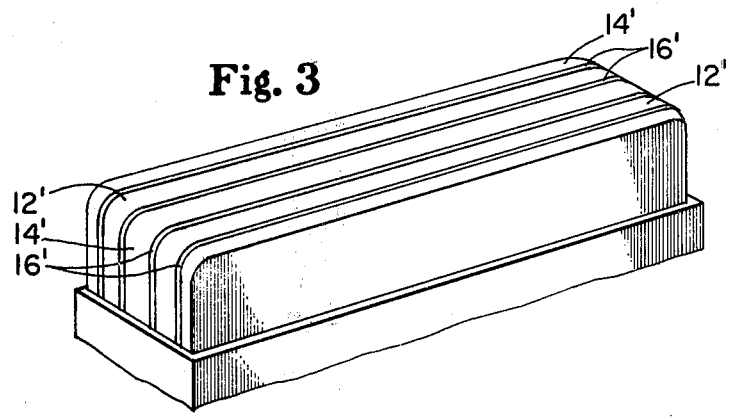
FIG. 3 is a fragmentary perspective view of another embodiment of the invention.
Figure 4:
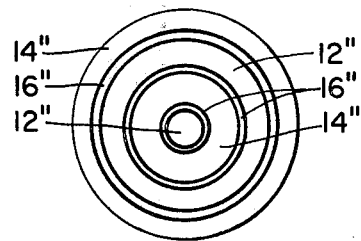
FIG. 4 is a plan view of yet another embodiment of the invention.

In other embodiments of the present invention, shown and illustrated in FIGS. 3 and 4, multiple phases can be used. For example, with reference to FIG. 3, multiple planar phases can be utilized, if desired. Hence, a generally rectangular stick can comprise antiperspirant phases 12', gel phases 14' and barrier phases 16'. Additionally, for example, with reference to FIG. 4, multiple concentric phases can be utilized, if desired. Thus, a generally circular stick can comprise antiperspirant phases 12'', gel phases 14'' and barrier phase 16''.

COMPOSITION USE

The three-phase antiperspirant sticks of the present invention are used to inhibit axillary perspiration in the same manner as any conventional antiperspirant stick composition. The present stick compositions can be easily applied to the skin leaving little or no perceptible residue. Such sticks further provide cosmetically desirable application characteristics such as glidability and coolness not generally provided by single phase stick composition.

The three-phase antiperspirant stick compositions herein are generally marketed in combination with some type of conventional packaging or dispensing means. Such means can include handles, wrappers, tubes, extruding devices (FIG. 2) and the like.

The three-phase antiperspirant sticks of the present invention are illustrated by the following examples:

EXAMPLE I

A three-phase antiperspirant stick of the following composition is prepared.

| Component | | Wt.% |
|---|---|---|
| A. Antiperspirant Core | | 48% |
| Ingredient | % by Weight | |
| Ozokerite wax | 5.0% | |
| Cetyl alcohol | 9.5% | |
| Isopropyl palmitate | 37.5% | |
| Aluminum chlorhydroxide particles [Al$_2$(OH)$_5$Cl . 2H$_2$O] | 43.5% | |
| Perfume | 0.5% | |
| *Cab-O-Sil (grade M-5) | 4.0% | |
| | 100.0% | |
| B. Gel-Phase Shell | | 48% |
| Ingredient | % by Weight | |
| Ethanol | 69% | |
| Sodium Stearate | 7.5% | |
| Propylene glycol | 20.00% | |
| FD&C Blue #1 (coloring: 0.5% aqueous solution) | 0.25% | |
| Perfume | 0.80% | |
| Water | 2.45% | |
| | 100.00% | |
| C. Barrier Phase Sleeve (Thickness: 0.020 inches) | | 4% |
| Ingredient | % by Weight | |
| Ozokerite Wax | 30% | |
| Stearyl Alcohol | 16.9% | |
| **Fluid AP ® (Propylene oxide/ butyl alcohol condensate) | 53.1% | |
| | 100.0% | 100.0% |

*A pyrogenic silica (Cabot Corp.) having a particulate diameter between about 0.01 and 0.03 microns as disclosed in British Patent 987,301 and British Patent 1,167,173.
**Butyl alcohol condensate with about 14 moles of propylene oxide marketed by Union Carbide Corp.

In Example I, the stick is prepared by first forming the antiperspirant core by charging a steel vessel with the ozokerite wax, cetyl alcohol, and isopropyl myristate and heating to approximately 200° F. with moderate agitation until these components are well intermixed. Next, the cab-o-sil is stirred into the mixture and is dispersed therein. Thereafter, the aluminum chlorhydroxide powder is likewise stirred into the mixture and is dispersed therein. This mixture is then allowed to cool to just above the solidification temperature at which point the perfume is stirred into the mixture. The molten mixture is finally poured into the cylindrical mold; is allowed to solidify by cooling to room temperature; and thereafter is removed from the mold to form the antiperspirant cores of the present invention.

The barrier phase components of ozokerite wax, stearyl alcohol and Fluid AP ® of the specified proportions are charged to a second steel vessel and are heated with moderate agitation until well intermixed. The antiperspirant cores prepared as described above are dipped for about one second into the molten barrier phase mixture and then are withdrawn. The antiperspirant core/barrier sleeve pieces are then allowed to cool to room temperature.

The gel phase components are charged into a third steel vessel equipped with a reflux condenser with the ethanol and the propylene glycol, and then are heated with moderate agitation until the mixture begins to boil and reflux. Thereafter, sodium stearate is added. The heating and agitation is continued until the sodium stearate is completely dissolved. Next, the optional components comprising water, the FD&C Blue #1, and the perfume are added while maintaining the agitation and refluxing. The molten gel material is then poured into the annular space of a suitable cylindrical mold into which had been centered the previously prepared antiperspirant core/barrier phase piece. The molten gel is allowed to solidify to form the shell of the three-phase stick of the present invention.

The stick so produced is an effective antiperspirant composition in the form of a three-phase stick. The stick exhibits minimal syneresis and interfacial interaction and provides cosmetically desirable application characteristics when applied to the skin.

Sticks of substantially similar physical/cosmetic character and antiperspirant effectiveness are realized when in the Example I stick the isopropyl palmitate of the antiperspirant core is replaced with an equivalent amount of isopropyl myristate, cetyl acetate, cetyl propionate, di-n-butyl phthalate, diethyl sebacate, diisopropyl adipate, ethyl carbomethyl phthalate, Fluid AP ® (Butyl alcohol condensed with about 14 moles of propylene oxide) or DCC-225 Fluid (dimethyl siloxane polymer of viscosity 9.5 cs. at 25° C. marketed by Dow Corning Corp.).

Compositions of substantially similar physical/cosmetic character and antiperspirant effectiveness are realized when in the Example I stick the sodium stearate of the gel phase shell is replaced with an equivalent amount of sodium palmitate, sodium myristate, potassium palmitate or potassium stearate.

EXAMPLE II

A three-phase antiperspirant stick of the following composition is prepared:

| Component | | Wt.% |
|---|---|---|
| A. Antiperspirant Core | | 42% |
| Ingredient | % by Weight | |
| Ceresin | 8.5% | |
| Stearyl alcohol | 10.0% | |
| Fluid AP ® (Propylene oxide/butyl alcohol condensate) | 35.9% | |
| *ZAG (antiperspirant active powder) | 45.6% | |
| | 100.0% | |
| B. Gel-Phase Shell | | 56% |
| Ingredient | % by Weight | |
| Sodium stearate | 7.0% | |
| Propylene glycol | 91.94% | |
| FD&C Blue #1 (coloring) | 0.26% | |
| Perfume | 0.80% | |
| | 100.0% | |
| C. Barrier Phase Sleeve (Thickness 0.010 inch) | | 2% |
| Ingredient | % by Weight | |
| Paraffin | 10% | |
| Myristyl alcohol | 30% | |
| Isopropyl myristate | 60% | |
| | 100% | 100% |

*ZAG is a complex formed from ZrO(OH)Cl . 3H$_2$O; Al$_2$(OH)$_5$Cl . 2H$_2$O and glycine in accordance with Luedders et al, U.S. Pat. No. 3,792,068, issued February 12, 1974. Particle Size Range = 1–44 microns.

Such a stick is prepared in a manner similar to that described in Example I. The stick so produced is an effective antiperspirant composition in the form of a three-phase stick. The composition exhibits minimal interfacial interaction and glides easily onto the skin during application.

Stick compositions of substantially similar physical/cosmetic character and antiperspirant effectiveness are realized when in the Example II stick composition the ceresin wax of the antiperspirant core is replaced with an equivalent amount of ozokerite, white beeswax or carnauba wax.

Compositions of substantially similar physical/cosmetic character and antiperspirant effectiveness are realized when in the Example II composition the propylene glycol of the gel phase is replaced with an equal amount of glycerine, ethylene glycol, or trimethylene glycol.

Compositions of substantially similar stability are realized when in the barrier phase of the Example II composition the paraffin is replaced with an equal amount of ceresin or ozokerite.

EXAMPLE III

A three-phase antiperspirant stick composition of the following composition is prepared:

| Component | | Wt.% |
|---|---|---|
| A. Antiperspirant Core | | 56% |
| Ingredient | % by Weight | |
| Carnauba wax | 10.0% | |
| Beeswax | 5.0% | |
| Stearyl alcohol | 7.0% | |
| Isopropyl myristate | 24.0 | |
| DC-556* | 10.0% | |
| Aluminum chlorhydroxide | 40.0% | |
| Aluminum chloride mixture** (ACH/AC wt. ratio = 3:1) | | |
| Perfume | 1.0% | |
| Bentone 38 ® | 3.0% | |
| | 100.0% | |
| B. Gel-Phase Shell | | 42% |
| Ingredient | % by Weight | |
| Potassium Stearate | 10.0% | |
| Ethanol | 60.55% | |
| Propylene glycol | 29.0% | |
| FD&C Blue #1 (coloring, 0.5% aqueous solution) | 0.15% | |
| Triclosan*** (deodorant) | 1.0% | |
| Klucel ® (antisyneresis agent) | 0.5% | |
| Perfume | 0.8% | |
| | 100.0% | |
| C. Barrier Phase Sleeve (Thickness: 0.010 inch) | | 2% |

-continued

| Component | Wt.% |
|---|---|
| Ingredient | % by Weight |
| Ceresin | 30% |
| Isopropyl palmitate | 70% |
| | 100%       100% |

*DC-556 in tris (trimethylsiloxy) phenylsilane marketed by Dow Corning Corporation.
**Aluminum chlorhydroxide is $Al_2(OH)_5Cl \cdot 2H_2O$ Aluminum Chloride is $AlCl_3 \cdot 6H_2O$
***2 hydroxy 2'-4, 4' trichlorodiphenyl oxide supplied by Ciba-Geigy Corp.

Such a stick is prepared in a manner similar to that described in Example I. The stick so produced is an effective antiperspirant/deodorant composition in the form of a three-phase stick. The composition exhibits minimal interfacial interaction and provides a cooling sensation when applied to the skin.

Stick compositions of substantially similar physical/cosmetic character and antiperspirant/deodorant effectiveness are realized when, in the Example III composition, the stearyl alcohol of the antiperspirant core is replaced with an equivalent amount of cetyl alcohol, myristyl alcohol, lauryl alcohol or glycerol monostearate.

Stick compositions of substantially similar physical/cosmetic character and antiperspirant/deodorant effectiveness are realized when, in the Example III composition, the aluminum chlorhydroxide/aluminum chloride mixture is replaced with an equivalent amount of a particulate antiperspirant active material selected from the group consisting of ZAG complexes wherein the zirconium compound is $ZrO(OH)_{2-a}Cl_a \cdot nH_2O$ with $a = 1.5$ to $1.87$ and $n = 1$ to 7; the aluminum compound is $Al_2(OH)_5Cl \cdot 2H_2O$ and the amino acid compound is glycine: That is, the above represents any aluminum/zirconium/chlorhydroxide salt having an Al:Zr molar ratio range of about 1.67 to 12.5 and a Metal:Cl molar ratio range of about 0.73 to 1.93.

Stick compositions of substantially similar physical/cosmetic character and antiperspirant/deodorant effectiveness are realized when in the Example III stick compositions the ethanol of the gel phase is replaced by an equivalent amount of methanol, isopropanol, or n-propanol.

INTERFACIAL INTERACTION EVALUATION

As noted above, a barrier phase of specified composition which is relatively free of particualte material and has a specified minimum thickness is essential to the realization of antiperspirant sticks which are not subject to degradation by interfacial interaction. The importance of such essential elements of the barrier phase can be demonstrated by formulating stick compositions with barrier phases containing various types of waxes and by formulating stick compositions with barrier phases containing various particulate materials such as talc, particulate active, and kaolin, and then observing such compositions after a one week storage at 120° F. Those compositions subject to interfacial interaction can be identified by the presence of a liquid runoff present in the bottom of the container holding the three-phase sticks and/or plasticization of the antiperspirant core phase. Further visual evidence of interfacial interaction is the shrinking of both the gel and the antiperspirant phases.

Storage at 120° F. is a relatively harsh test condition. Even barrier-free sticks which would remain stable under milder test conditions (e.g., room temperature) for as long as two months might show appreciable interfacial interaction after only the one week at the elevated 120° F. storage temperature. Thus, sticks which do not exhibit interfacial interaction after one week at the elevated temperature storage are very stable sticks. Of course, it is realized that prolonged storage at elevated temperatures or storage at even higher temperatures will induce degradation in even the barrier-containing sticks of the present invention.

Several stick compositions are selected for such interfacial interaction evaluation at 120° F. for one week. The compositions tested are those described in Table I.

TABLE I

| | | Experience Interfacial Interaction | | | | | Do Not Experience Interfacial Interaction | | | | | |
|---|---|---|---|---|---|---|---|---|---|---|---|---|
| | | Percent By Weight of Phase | | | | | | | | | | |
| | Ingredients | A | B | C | D | E | F | G | H | I | J | K | L |
| GEL PHASE | Sodium Stearate | 5 | 6 | 7 | 8 | 9 | 9 | 9 | 7 | 6 | 7 | 8 | 9 |
| (49% by wt. of stick) | Ethanol | 80 | 77 | 12 | 74 | 31 | 67 | 67 | 70 | 32 | 70 | 40 | 67 |
| | Propylene Glycol | 13 | 15 | 80 | 17 | 60 | 22 | 22 | 21 | 60 | 21 | 50 | 22 |
| | Optionals | 2 | 2 | 1 | 1 | — | 2 | 2 | 2 | 2 | 2 | 2 | 2 |
| | | 100 | 100 | 100 | 100 | 100 | 100 | 100 | 100 | 100 | 100 | 100 | 100 |
| ANTIPERSPIRANT PHASE | Ozokerite | 9 | 8 | 7 | 7 | 7 | 7 | 7 | 9 | 8 | 7 | 6 | 7 |
| (49% by wt. of stick) | Stearyl alcohol | 5 | 15 | 0 | 0 | 0 | 0 | 0 | 5 | 0 | 0 | 4 | 0 |
| | Isopropyl Palmitate | 26 | 32 | 38 | 38 | 48 | 48 | 48 | 26 | 32 | 38 | 40 | 48 |
| | Aluminum Chlorhydroxide | 50 | 35 | 45 | 45 | 35 | 35 | 35 | 50 | 50 | 45 | 40 | 35 |
| | Optionals | 10 | 10 | 10 | 10 | 10 | 10 | 10 | 10 | 10 | 10 | 10 | 10 |
| | | 100 | 100 | 100 | 100 | 100 | 100 | 100 | 100 | 100 | 100 | 100 | 100 |
| BARRIER PHASE | Ozokerite | — | — | 10 | 15 | 30 | 0 | 10 | 15 | 30 | 20 | 20 | 20 |
| (Thickness: .020 in. | Beeswax | — | — | 0 | 0 | 0 | 15 | 0 | 0 | 0 | 0 | 0 | 0 |
| 2% by wt. of stick) | Stearyl Alcohol | — | — | 30 | 17 | 17 | 17 | 30 | 17 | 17 | 10 | 20 | 30 |
| | Isopropyl Palmitate | — | — | 27 | 30 | 24 | 40 | 30 | 38 | 28 | 30 | 35 | 40 |
| | Fluid AP ® | — | — | 25 | 28 | 23 | 28 | 30 | 28 | 25 | 40 | 25 | 10 |
| | Talc | — | — | 8 | 10 | 0 | 0 | 0 | 0 | 0 | 0 | 0 | 0 |
| | ZAG | — | — | 0 | 0 | 6 | 0 | 0 | 2 | 0 | 0 | 0 | 0 |
| | | | | 100 | 100 | 100 | 100 | 100 | 100 | 100 | 100 | 100 | 100 |

As can be seen from the above Table I, compositions A through E exhibit interfacial interaction while compositions F through J do not exhibit such degradation. Compositions F-J represent compositions of the present invention inasmuch as these compositions contain a barrier phase of the requisite composition, minimum thickness and which is relatively free of particulate materials. Compositions A-E either do not contain a barrier phase or have a barrier phase either containing a high melting point wax which is soluble in the gelling solution or containing significant amounts of particulate materials. These compositions without barriers or with defective barriers are thus subject to interfacial interaction.

What is claimed is:

1. An antiperspirant composition in the form of a three-phase stick, said composition comprising:
   (A) from about 35% to 65% by weight of the composition of an antiperspirant phase comprising a solid, shearable vehicle which contains an astringent antiperspirant material;
   (B) from about 35% to 65% by weight of the composition of a gel phase, said gel phase comprising
      I. from about 10% to 92% by weight of the gel phase of a polyhydric aliphatic alcohol containing 2 to 3 carbon atoms and from 2 to 3 hydroxy groups;
      II. from about 5% to 15% by weight of the gel phase of a gel forming agent selected from the group consisting of a sodium salt of a fatty acid containing 14 to about 18 carbon atoms and a potassium salt of a fatty acid containing from about 14 to about 18 carbon atoms; and
   (C) from about 1% to 10% by weight of the composition of an interjacent barrier phase contiguous to the gel phase and the antiperspirant phase, wherein the barrier phase has a thickness of at least about 0.005 inch and comprises:
      I. from about 10% to 40% by weight of the barrier phase of a water-insoluble, alcohol-insoluble high melting point wax or mixtures thereof which has a melting point of from about 150° F. to 215° F.; and
      II. from about 20% to 90% by weight of the barrier phase of a water-insoluble, liquid organic emollient,
   and wherein the barrier phase is relatively free of particulate materials and is free of materials capable of reducing the pH of the gel phase below about 9.5 in the region of the gel/barrier interface.

2. A composition in accordance with claim 1 wherein
   (A) the antiperspirant phase comprises
      I. from about 2% to 15% by weight of the antiperspirant phase of a water-insoluble high melting wax or mixtures thereof which has a melting point of from about 150° F. to 215° F.
      II. from about 20% to 50% by weight of the antiperspirant phase of a water-insoluble liquid, organic, emollient; and
      III. from about 11% to 50% by weight, on an anhydrous basis, of the antiperspirant phase of a solid particulate astringent antiperspirant material; and,
   (B) wherein the gel phase additionally contains from about 10% to 72% by weight of gel phase of a monohydric alcohol selected from the group consisting of methanol, ethanol, isopropanol, and n-propanol, and wherein the weight ratio of polyhydric alcohol to gel-forming agent in the gel phase exceeds about 2.45.

3. A composition in accordance with claim 2 wherein the antiperspirant phase comprises a core, the barrier phase comprises a sleeve surrounding the antiperspirant phase barrier and the gel phase comprises a shell surrounding said phase.

4. A composition in accordance with claim 2 wherein the barrier phase ranges in thickness of from about 0.010 inch to 0.040 inch and contains no more than about 5.0% of particulate materials having a particle size of greater than about one micron.

5. A composition in accordance with claim 4 wherein
   (A) the high melting wax comprises from about 3% to 11% by weight of the antiperspirant phase and is selected from the group consisting of beeswax, carnauba, bayberry, candelilla, montan, ozokerite, ceresin, paraffin, Fisher-Tropsch waxes, microcrystalline waxes and mixtures thereof;
   (B) the organic emollient comprises from about 30% to 40% by weight of the antiperspirant phase and is selected from the group consisting of isopropyl myristate, isopropyl palmitate, cetyl acetate, cetyl propionate, di-n-butyl phthalate, diethyl sebacate, diisopropyl adipate, ethyl carbomethyl phthalate, the condensation product of about 14 moles of propylene oxide with one mole of butyl alcohol, and polydimethylsiloxanes having a viscosity of from about 9 to 50 cs. at 25° C.;
   (C) the particulate antiperspirant material comprises from about 30% to 46% by weight on an anhydrous metal salt basis (exclusive of complexing agents) of the antiperspirant phase and is selected from the group consisting of
      (i) aluminum hydroxyhalides of the empirical formula $Al_2(OH)_xQ_y \cdot XH_2O$ wherein Q is selected from the group consisting of chlorine, bromine and iodine, wherein X is from 2 to 5 and $x+y=6$ and wherein X is 1 to 6; and
      (ii) zirconium/aluminum/amino acid complexes which contain
         (a) one part of an aluminum compound of the formula $Al_2(OH)_{6-m}Q_m \cdot YH_2O$ wherein Q is selected from the group consisting of chloride, bromide and iodide; m is a number from about 0.8 to 2.0 and Y is 1 to 6;
         (b) x parts of a zirconium compound of the formula $ZrO(OH)_{2-a}Q_a \cdot nH_2O$ wherein Q is selected from the group consisting of chloride, bromide and iodide; wherein a is from 1 to 2, wherein n is from 1 to 8 and wherein x is from about 0.16 to about 1.2; and
         (c) p parts neutral amino acid selected from the group consisting of glycine, dl-tryptophane, dl-β-phenylalanine, dl-valine, dl-methionine and β-alanine, and wherein p has a value of from about 0.06 to about 0.53;
   (D) the polyhydric aliphatic alcohol comprises from about 15% to 50% by weight of the gel phase and is selected from the group consisting of ethylene glycol, propylene glycol, trimethylene glycol, and glycerine;
   (E) the monohydric alcohol comprises from about 40% to 70% by weight of the gel phase and is selected from the group consisting of ethanol and isopropanol;
   (F) the water insoluble, alcohol-insoluble high melting point wax of the barrier phase comprises from about 20% to 40% by weight of the barrier phase and is selected from the group consisting of paraffin, ozokerite and ceresin; and
   (G) the barrier phase further comprises from about 10% to 30% by weight of the barrier phase of a low melting point wax or mixtures thereof having a melting point of from about 100° F. to 150° F.

6. A composition in accordance with claim 5 wherein the gel-forming agent comprises from about 7% to 10% by weight of the gel phase and is selected from the group consisting of sodium stearate, sodium palmitate, sodium myristate, potassium stearate and potassium palmitate.

7. A composition in accordance with claim 5 wherein the low melting point wax is selected from the group consisting of cetyl alcohol, stearyl alcohol, myristyl alcohol, lauryl alcohol and glyceryl monostearate.

8. A composition in accordance with claim 5 wherein the antiperspirant core contains an additional component selected from the group consisting of
(A) from about 2% to 20% by weight of antiperspirant core of a low melting point wax or mixtures thereof having a melting point of from about 100° F. up to 150° F.;
(B) from about 0.5% to 5% by weight of antiperspirant core of an inert filler material; and
(C) combinations of both said low melting point wax and said inert filler.

9. A composition in accordance with claim 5 wherein the gel phase shell contains an additional component selected from the group consisting of
(A) from about 0.1% to 1.0% by weight of gel phase shell of a deodorant material;
(B) from about 0.1% to 5.0% by weight of gel phase shell of an antisyneresis/evaporation retardant selected from the group consisting of a carboxyalkylcellulose and a hydroxyalkylcellulose; and
(C) combinations of both said deodorant material and said antisyneresis/evaporation retardant.

10. A composition in accordance with claim 5 wherein
(A) the high melting point wax is selected from the group consisting of ceresin, beeswax, ozokerite and a synthetic wax;
(B) the emollient is selected from the group consisting of isopropyl myristate, isopropyl palmitate, the condensation product of about 14 moles of propylene oxide with butyl alcohol and polydimethylsiloxanes having a viscosity of from about 9 to 50 cs. at 25° C.;
(C) the antiperspirant material is in impalpable particulate form and is selected from the group consisting of
 (i) $Al_2(OH)_5Cl \cdot 2H_2O$
 (ii) mixtures of $AlCl_3 \cdot 6H_2O$ and $Al_2(OH)_5Cl \cdot 2H_2O$ in an aluminum chloride to aluminum hydroxychloride weight ratio of up to 0.5;
 (iii) zirconium/aluminum/glycine complexes containing about one part $Al_2(OH)_5Cl \cdot 2H_2O$; x parts of $ZrO(OH)Cl \cdot 3H_2O$ and p parts glycine wherein x is from about 0.16 to 1.2 and p is from about 0.06 to 0.53; and
 (iv) zirconium/aluminum/glycine complexes containing about one part $Al_2(OH)_5Cl \cdot 2H_2O$; x parts of $ZrO(OH)_{2-a}Cl_a \cdot nH_2O$; and p parts glycine wherein a is from about 1.5 to 1.87, n is 1 to 7, x is from about 0.16 to 1.2 and p is from about 0.06 to 0.53;

(D) the polyhydric alcohol is propylene glycol; and
(E) the gel forming agent comprises from about 7% to 10% by weight of the gel phase and is selected from the group consisting of sodium stearate, sodium palmitate, sodium myristate, potassium stearate and potassium palmitate.

11. A composition in accordance with claim 10 which contains an additional component selected from the group consisting of
(A) from about 5% to 15% by weight of the antiperspirant core of low melting point wax present in the antiperspirant core, said low melting point wax being selected from the group consisting of cetyl alcohol, stearyl alcohol, myristyl alcohol, lauryl alcohol and glycerol monostearate;
(B) from about 0.5% to 5% by weight of the antiperspirant core of an inert filler present in said antiperspirant core, said filler being selected from the group consisting of talc, a colloidal silica and a hydrophobic clay;
(c) from about 0.1% to 5.0% by weight of the gel phase shell of an anti-syneresis agent present in said gel phase shell, said anti-syneresis agent comprising hydroxypropylcellulose compounds having molecular weights ranging from about 60,000 to 1,000,000;
(D) from about 0.1% to 1.0% by weight of the gel phase shell of a deodorant material present in said gel phase shell, said deodorant material being selected from the group consisting of a bacteriostatic quaternary ammonium compound, a metal salt of a monohydroxybenzene sulfonic acid, a halogenated dihydroxydiphenyl methane and a derivative of 1,3-diphenylurea having one or more hydrogen atoms replaced with halogen; and
(E) various combinations of said additional components.

12. A rub-on antiperspirant stick comprising a plurality of chemically dissimilar active phases and a barrier phase interposed therebetween to preclude interaction of said active phases while contained within the antiperspirant stick, a transverse section across said active and barrier phases defining an application surface to be rubbed across a skin surface to provide antiperspirant protection thereto, each of said active and barrier phases being compounded and arranged to provide substantially equal shear rates so that they wear at approximately the same rate during rubbing of said application surface across the skin being treated, thereby reducing undesirable phase protrusion as the stick is worn away inward of the application surface during use.

13. A composition in accordance with claim 3 wherein the core and sleeve phase are of dissimilar color.

* * * * *